(12) United States Patent
Matteucci et al.

(10) Patent No.: US 10,456,729 B2
(45) Date of Patent: Oct. 29, 2019

(54) PROCESS FOR CARBON DIOXIDE RECOVERY FROM A GAS STREAM CONTAINING CARBON DIOXIDE AND HYDROCARBONS

(71) Applicant: Dow Global Technologies LLC, Midland, MI (US)

(72) Inventors: Scott T. Matteucci, Midland, MI (US); Ajay N. Badhwar, Houston, TX (US); H. Robert Goltz, Midland, MI (US); Jonathan W. Leister, Manvel, TX (US); Nicholas J. Shurgott, Rosharon, TX (US)

(73) Assignee: Dow Global Technologies LLC, Midland, MI (US)

( * ) Notice: Subject to any disclaimer, the term of this patent is extended or adjusted under 35 U.S.C. 154(b) by 236 days.

(21) Appl. No.: 15/328,546

(22) PCT Filed: Aug. 5, 2014

(86) PCT No.: PCT/US2014/049797
§ 371 (c)(1),
(2) Date: Jan. 24, 2017

(87) PCT Pub. No.: WO2016/018437
PCT Pub. Date: Feb. 4, 2016

(65) Prior Publication Data
US 2017/0216759 A1   Aug. 3, 2017

Related U.S. Application Data

(60) Provisional application No. 62/030,362, filed on Jul. 29, 2014.

(51) Int. Cl.
*E21B 43/16* (2006.01)
*B01D 53/04* (2006.01)
(Continued)

(52) U.S. Cl.
CPC .............. *B01D 53/04* (2013.01); *B01J 20/20* (2013.01); *B01J 20/267* (2013.01); *B01J 20/28064* (2013.01); *B01J 20/3078* (2013.01); *B01J 20/3085* (2013.01); *B01J 20/3416* (2013.01); *B01J 20/3425* (2013.01); *B01J 20/3441* (2013.01); *B01J 20/3483* (2013.01); *B01J 20/3491* (2013.01); *C01B 32/50* (2017.08);
(Continued)

(58) Field of Classification Search
CPC ............ Y02B 10/08; B01D 53/04; C07C 7/12
See application file for complete search history.

(56) References Cited

U.S. PATENT DOCUMENTS 3,065,790 A   11/1962   Holm
3,150,716 A   9/1964   Strelzoff et al.
(Continued)

*Primary Examiner* — Angela M DiTrani Leff

(57) ABSTRACT

A process for purification of a carbon dioxide feedstock that includes carbon dioxide and gaseous and liquid $C_1+$ hydrocarbons. Specifically, a carbon dioxide feedstream is passed through one or more separation unit, each separation unit removing one or more $C_1+$ hydrocarbon from the carbon dioxide feedstream to provide a richer carbon dioxide gas stream. The one or more separation unit employs an adsorption media and has an adsorption step and a media regeneration step.

5 Claims, 9 Drawing Sheets

(51) Int. Cl.
  *E21B 43/40* (2006.01)
  *B01J 20/20* (2006.01)
  *B01J 20/26* (2006.01)
  *B01J 20/28* (2006.01)
  *B01J 20/30* (2006.01)
  *B01J 20/34* (2006.01)
  *C07C 7/12* (2006.01)
  *C01B 32/50* (2017.01)

(52) U.S. Cl.
  CPC .............. *C07C 7/12* (2013.01); *E21B 43/164* (2013.01); *E21B 43/40* (2013.01); *B01D 2253/202* (2013.01); *B01D 2256/22* (2013.01); *B01D 2256/24* (2013.01); *B01D 2256/245* (2013.01); *B01D 2257/504* (2013.01); *B01D 2257/702* (2013.01); *C01B 2210/007* (2013.01); *C01B 2210/0015* (2013.01); *C01P 2006/80* (2013.01); *Y02C 10/08* (2013.01); *Y02P 90/70* (2015.11)

(56) References Cited

U.S. PATENT DOCUMENTS

| | | | |
|---|---|---|---|
| 4,000,990 A | * | 1/1977 | Bingham ........... B01D 53/0476 95/103 |
| 4,333,529 A | | 6/1982 | McCorquodale |
| 4,344,486 A | | 8/1982 | Parrish |
| 4,762,543 A | | 8/1988 | Pantermuehl et al. |
| 5,288,307 A | * | 2/1994 | Goltz ...................... B01J 20/26 95/143 |
| 6,505,683 B2 | | 1/2003 | Minkkinen et al. |

\* cited by examiner

PROCESS FOR CARBON DIOXIDE RECOVERY FROM A GAS STREAM CONTAINING CARBON DIOXIDE AND HYDROCARBONS

FIELD OF THE INVENTION

The invention relates to a process for purification of a feedstock that contains carbon dioxide and gaseous and liquid hydrocarbons that are recovered from at least one production well operating with an injection of carbon dioxide.

BACKGROUND OF THE INVENTION

The assisted recovery of petroleum is commonly used in the petroleum industry to recover crude oil that remains in place in a formation after its natural or forced production or to recover heavy fuel that is too viscous to flow naturally or artificially using unsophisticated pumping means. Traditionally, steam was the driving force that was most commonly used to flush crude oil formations effectively, but production programs have increasingly implemented an injection of carbon dioxide ($CO_2$) to produce petroleum. Carbon dioxide has proven to be a particularly advantageous gas, to the extent that it can be used by the producers for the assisted recovery of petroleum.

Injection of $CO_2$ specifically for the purpose of increasing hydrocarbon production, is known as Enhanced Oil Recovery (EOR) or "assisted recovery", see U.S. Pat. Nos. 4,333,529; 3,065,790; and 3,150,716. Carbon dioxide is introduced into an injection well proves effective for reducing the viscosity of the petroleum in place and for increasing its mobility, which facilitates its recovery.

Desirably, the recovered $CO_2$ from a production well can be reinjected via an injection well to reduce the viscosity of the petroleum in place in a formation. However, a non-negligible portion of $CO_2$ is sequestered in the formation and irretrievably lost, a portion of the injected carbon dioxide is dissolved in the crude oil solution and can therefore be recovered with the petroleum during its production to be recycled later, and the remaining $CO_2$ stream that is recovered from a production well contains hydrocarbons.

The recovered $CO_2$ stream is a gaseous and liquid stream that is under pressure and typically is separated in gas-liquid separators, to obtain a liquid phase of propane and heavier hydrocarbons ($C_3$+ hydrocarbons), and a gaseous phase containing primarily $CO_2$ and a substantial amount of impurities of methane ($C_1$) with a little less ethane ($C_2$). These impurities can represent 5 to 12 mol percent of the separated gaseous phase. In some cases where acidic crude oils are produced, the associated gas can also contain the hydrogen sulfide ($H_2S$) that is found in part as an impurity (several percent, for example). The processes of U.S. Pat. No. 4,762,543 and US Patent Application No.: 2002/0036086 are directed to a process for removal of such components from the produced $CO_2$ prior to its reinjection.

Another possibility would be to reinject the impure $CO_2$ stream that contains methane and ethane into the formation, such action would deleteriously affect the saturation pressure of the formation. Other possibilities would be to mix impure $CO_2$ stream with pure $CO_2$ obtained from an outside source, or with other hydrocarbons that are heavier than the impurities in such a way as to dilute it and to counterbalance the volatility of the methane, but these technical solutions are very costly.

Cryogenic distillation could also be used to extract the methane and the ethane from $CO_2$ and then the separated $CO_2$ could be recycled into the formation. This separation, however, also proves to be very expensive.

Solvents exist that can absorb $CO_2$, preferably with hydrocarbons, but these solvents would very easily absorb the hydrogen sulfide that is present, which would produce $CO_2$ that is polluted by $H_2S$.

U.S. Pat. No. 4,344,486 teaches hydrocarbons that contaminate carbon dioxide can be combusted by an oxygen-enriched gas or by essentially pure oxygen.

There exists a need for an effective and inexpensive separation technique that is capable of removing the full range of hydrocarbons without adding new contaminates.

SUMMARY OF THE INVENTION

A first object of the invention is a process to separate carbon dioxide from hydrocarbon impurities that it contains.

A second object is a process to recycle this essentially pure carbon dioxide in an injection well so as to implement a process for assisted recovery of petroleum that is contained in a formation.

One embodiment of the present invention is a process to provide a carbon dioxide-rich gas stream from a carbon dioxide feedstream, preferably recovered from a production well, comprising one or more $C_1$+ hydrocarbon (i.e., one or more of methane, ethane, propane, butane, pentane, or heavier hydrocarbons), whereby the one or more $C_1$+ hydrocarbon is separated from the carbon dioxide feedstream to form a first treated carbon dioxide-rich gas stream by means of a first separation unit comprising: (i) a first adsorption unit comprising a first adsorption bed comprising a first adsorbent media, preferably a porous cross-linked polymeric adsorbent, which adsorbs one or more $C_1$+ hydrocarbon, preferably $C_3$+ hydrocarbons, to form a loaded first adsorbent media and (ii) a first regeneration unit comprising a means to regenerate the loaded first adsorbent media by causing the release of the adsorbed one or more $C_1$+ hydrocarbon from the loaded first adsorbing media and forming regenerated first adsorbent media wherein the process comprises the steps of: (a) passing the carbon dioxide feedstream through the first adsorption unit of the first separation unit at a first flow rate generating a loaded first adsorbent media comprising one or more $C_1$+ hydrocarbon and a first treated carbon dioxide-rich gas stream, (b) regenerating the loaded first adsorbent comprising one or more $C_1$+ hydrocarbon by releasing the adsorbed one or more $C_1$+ hydrocarbon from the loaded first adsorbing media and forming regenerated first adsorbent media, (c) recovering, further separating, using as fuel for a combustion process, flaring, or a combination thereof the released one or more $C_1$+ hydrocarbons, and (d) providing the first treated carbon dioxide-rich gas stream to one or more additional separation unit for further treatment, recovering the first treated carbon dioxide-rich treated gas stream, reinjecting the first treated carbon dioxide-rich treated gas stream into an injection well, or a combination thereof.

Another embodiment of the present invention is the process described herein above further comprising a second separation unit comprising: (iii) a second adsorption unit comprising a second adsorption bed comprising a second adsorbent media, preferably a pyrolized macroporous polymeric adsorbent, which adsorbs carbon dioxide and one or more $C_1$+ hydrocarbon, preferably $C_2$ and $CO_2$, to form a loaded second adsorbent media and (iv) a second regeneration unit comprising a means to regenerate the loaded second adsorbent media by causing the release of the adsorbed carbon dioxide and one or more $C_1+$ hydrocarbon from the loaded second adsorbing media and forming regenerated second adsorbent media further comprising the steps of: (e) passing the first treated carbon dioxide-rich gas stream through a second adsorption unit of the second separation unit at a second flow rate generating a methane-rich gas stream and a loaded second adsorbent media comprising one or more $C_1+$ hydrocarbon and carbon dioxide, (f) regenerating the loaded second adsorbent comprising one or more $C_1+$ hydrocarbon and carbon dioxide by releasing the adsorbed one or more $C_1+$ hydrocarbon and carbon dioxide from the loaded second adsorbing media and forming a regenerated second adsorbent media and a second treated carbon dioxide-rich gas stream, (g) providing the methane-rich gas stream to a natural gas pipeline for recovery, transportation, for use as fuel for a combustion process, for flaring, or a combination thereof, and (h) providing the second carbon dioxide-rich gas stream to one or more additional separation unit for further treatment, recovering the second carbon dioxide-rich gas stream, reinjecting the second treated carbon dioxide-rich treated gas stream into an injection well, or a combination thereof. Preferably, first adsorption media is not the same as the second adsorption media.

In one embodiment of the process of the present invention disclosed herein above, the adsorption media in each separation unit is independently regenerated by means of reduced pressure over the media, heating the media, or a combination of reduced pressure and heating, preferably heating is achieved using a microwave heating system.

Preferably in the process of the present invention disclosed herein above each regeneration step is operated independently as a batch process, a semi-continuous process, or as a continuous process.

Another embodiment of the present invention is the process described herein above further comprising a third separation unit comprising a condenser or a chiller further comprising the steps of: (i) passing the second treated carbon dioxide-rich gas stream through a third separation unit, (j) liquefying one or more $C_1+$ hydrocarbon, preferably $C_2$, from the second treated carbon dioxide-rich gas stream forming a third treated carbon dioxide-rich gas stream and one or more liquefied $C_1+$ hydrocarbon, (k) recovering the one or more liquefied $C_1+$ hydrocarbon for transportation, for use as fuel for a combustion process, for flaring, or a combination thereof, and (l) providing the third carbon dioxide-rich gas stream to one or more additional separation unit for further treatment, reinjecting the third treated carbon dioxide-rich treated gas stream into an injection well, or a combination thereof.

DETAILED DESCRIPTION OF THE PREFERRED EMBODIMENTS

Figure 1:
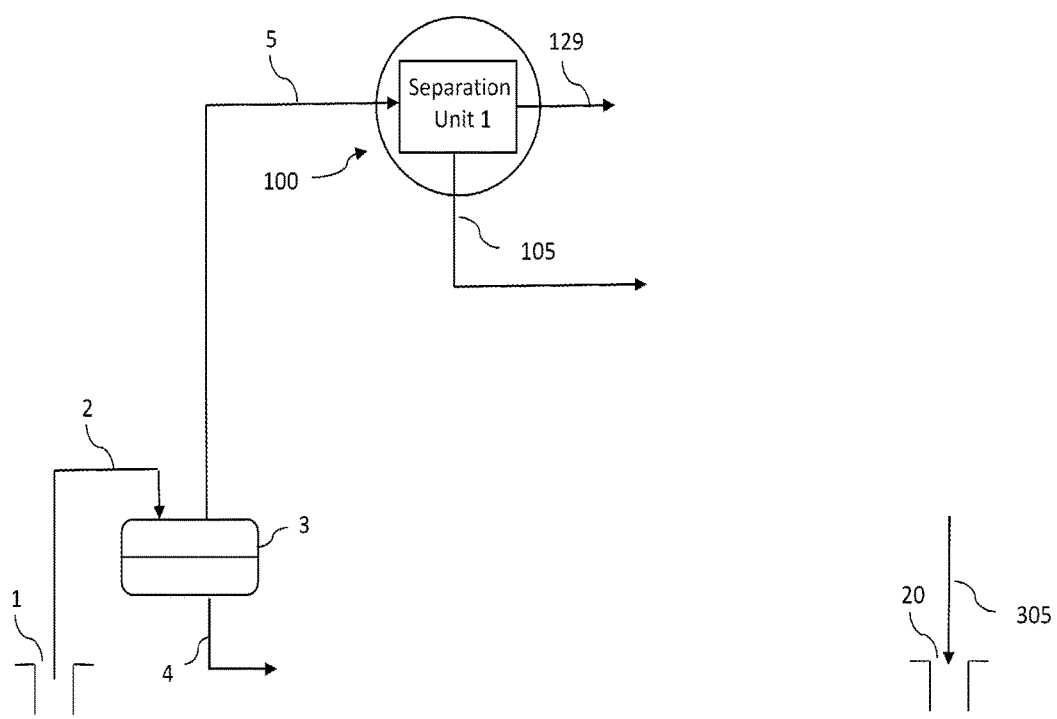
FIG. 1 is a schematic of a process of the present invention to remove $C_3+$ from a carbon dioxide feedstream from a production well.

There are a number of enhanced oil recovery systems available for increasing production from oil and gas reservoirs. These include steam injection, carbon dioxide and/or nitrogen gas flooding, waterflooding with chemicals such as polymers, surfactants, and alkalines, and the use of microbes to produce gases or chemicals underground that increase the mobility of remaining oil. Carbon dioxide ($CO_2$) flooding has proven to be among the most promising enhanced oil recovery methods for the United States because it takes advantage of plentiful, naturally-occurring carbon dioxide. When $CO_2$ is injected into a reservoir above its minimum miscibility pressure (a miscible flood), the gas acts as a solvent. The $CO_2$ picks up lighter hydrocarbon components, swelling the total volume of oil and reducing the viscosity of the oil so that it flows more easily. When a field has already been waterflooded, a tertiary $CO_2$ flood will normally provide incremental recovery of about 8 percent to about 16 percent of the original oil in place. When $CO_2$ is used instead of waterflood for secondary recovery, the field can produce up to about 40 percent of the original oil in place.

The injected $CO_2$ floods the treated zone and forces/carries the oil in the formation toward one or more production wells where the fluids are recovered. The composition of the produced fluids changes with time and, at some point, carbon dioxide "breakthrough" will occur. After breakthrough the volume of gas and the carbon dioxide content of the produced fluids increase substantially. Carbon dioxide may represent 60-96 mol percent (or more) of the fluids produced.

In order for $CO_2$ flooding operations to be economically viable, $CO_2$ must be efficiently recovered from the produced fluids for reuse. In many cases, recovered $CO_2$ can be reinjected into the formation through the injection well, provided chemical specifications for purity are met. Product specifications for $CO_2$ can be quite high, particularly with respect to the content of hydrocarbons, i.e., methane ($C_1$), ethane ($C_2$), and propane and higher ($C_3+$).

The terms "natural gas liquids" (NGL) and "ethane plus" ($C_2+$) refer broadly to hydrocarbons having two or more carbons such as ethane, propane, butane, and possibly small quantities of pentanes or heavier hydrocarbons.

The term "carbon dioxide rich" refers broadly to any $CO_2$ vapor or liquid stream from which at least some methane plus amounts have been recovered. Preferably, a carbon dioxide-rich gas stream has less than 85 mole percent of the $C_1+$ hydrocarbons.

The present invention is a process for separating the at least $C_3+$ hydrocarbons from a carbon dioxide gas stream. In one embodiment, the process of the present invention separates $C_1$ and $C_3+$ hydrocarbons from a carbon dioxide gas stream. In yet a further embodiment of the process of the present invention separates $C_1+$ hydrocarbons from a carbon dioxide gas stream.

The process of the present invention comprises one or more separation unit placed in series. Preferably, one or more separation unit comprises an adsorption bed that is filled with an adsorbent media that is able to remove one or more carbon dioxide, targeted hydrocarbon gas, and/or one or more targeted contaminant from a carbon dioxide gas stream.

Once the adsorbent has reached an appropriate degree of saturation with a target molecule, the adsorbent can either be transferred to a desorption chamber in a batch or continuous process, or the absorption chamber can be isolated to act as the desorption chamber. At such point, the saturated adsorbent can be regenerated by application of heat or pressure differential, where the heat can come from conductive heating, a heated purge gas or via microwave.

After desorption, the adsorbent can be transferred to the adsorption unit for subsequent use, or rendered unisolated from the initial feed stream such that the former desorption chamber becomes the adsorption chamber.

Furthermore this process allows for variation of adsorption systems for each targeted gas such that one separation system may be, for instance, a pressure swing adsorption to remove one target gas, while the next sorption system in series is a continuous microwave regeneration system, etc. As such, the invention does not require consistency between separations systems in terms of type or size.

The method of the present invention sequentially and/or selectively removes and recovers some or all $C_2+$(i.e., natural gas liquids) and $C_1$ (methane) from a carbon dioxide gas stream by the use of one or more separation units in series. Each separation unit comprises (i) an adsorption unit comprising an adsorption bed comprising an adsorbent media which adsorbs one or more hydrocarbon to form a loaded adsorbent media and (ii) a regeneration unit comprising a means to regenerate loaded adsorbent media by causing the release of adsorbed hydrocarbon(s) from the loaded adsorbing media and forming regenerated adsorbent media. The method of the present invention may utilize 1, 2, 3, 4, 5, 6, 7, 8, 9, or 10 separation units, or more for separating hydrocarbons from the carbon dioxide gas stream. In addition to the hydrocarbon separation units, the present invention may utilize one or more separation unit to remove one or more contaminant, for example there may be 1, 2, 3, 4, 5, 6, 7, 8, 9, 10, or more separation units for the removal of contaminants. The size and/or capacity of each separation unit is independent of the others and will depend, for example, on the targeted hydrocarbon or contaminant to be removed, the adsorbent composition, the regeneration process, the required gas purity leaving the separation system, the composition and fed rate of the feed gas, and the like.

One embodiment of the process of the present invention is shown in FIG. 1. A carbon dioxide rich gas stream 305 injected via at least one injection well 20 into a formation (not shown in the figure) produces under pressure from a production well 1 a gas/liquid (G/L) effluent 2 that comprises gaseous and liquid hydrocarbons and carbon dioxide. This gasses and liquids comprising the G/L effluent 2 are separated in a separator 3 with the liquids exiting the bottom of the separator via line 4 and the carbon dioxide gas feedstream, comprising carbon dioxide and one or more $C_1+$ hydrocarbons (i.e., one or more of methane, ethane, propane, butane, pentane, or heavier hydrocarbons), exits the top of the separator via line 5. Said carbon dioxide gas stream 5 is introduced into a first separation unit 100 containing the first adsorption media, preferably comprising a porous cross-linked polymeric adsorbent. The first adsorption media adsorbs one or more $C_1+$ hydrocarbon, preferably the hydrocarbons are $C_3+$ hydrocarbons, forming a loaded first adsorption media and a first treated carbon dioxide-rich gas stream comprising one or more $C_1+$ hydrocarbon 105, preferably the hydrocarbons are $C_1$ and $C_2$. The first loaded adsorption media is regenerated and the adsorbed ($C_3+$) hydrocarbons are released 129 and the first adsorption media is regenerated from the loaded first adsorption media. The released ($C_3+$) hydrocarbons 129 can be recovered, further separated, used as fuel for a combustion process, flared, or a combination thereof. The first treated carbon dioxide gas stream comprising one or more $C_1+$ hydrocarbon 105 can be supplied to one or more additional separation unit for further treatment, recovered, reinjected into an injection well, or a combination thereof. Water that is contained in the carbon dioxide gas stream may be eliminated before entering the first separation unit, for example if the separator 3 is a cooled condenser.

Figure 2:
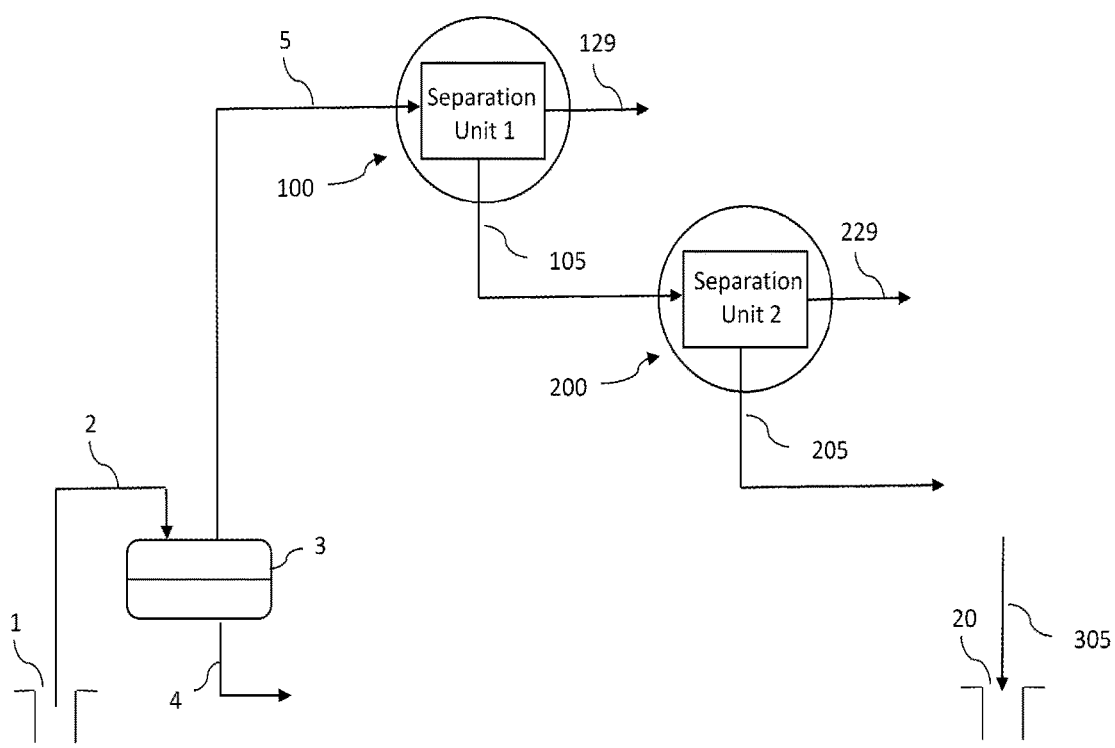
FIG. 2 is a schematic of a process of the present invention to sequentially remove $C_3+$ and $C_1$ from a carbon dioxide feedstream produced from a production well.

Referring now to FIG. 2, a second embodiment of the process of the present invention is shown. The gas stream 5 from the separator 3 is passed through the first separation unit 100 containing the first adsorption media, preferably comprising a porous cross-linked polymeric adsorbent, for the removal of one or more $C_1+$ hydrocarbon, preferably $C_3+$ hydrocarbons, 129 forming carbon dioxide-rich gas stream comprising one or more $C_1+$ hydrocarbons, preferably a $C_1$ and $C_2$, 105. Said first treated carbon dioxide-rich gas stream 105 is then passed through a second separation unit 200 containing a second adsorption media 202, preferably comprising a pyrolized macroporous polymers adsorbent. The second adsorption media adsorbs carbon dioxide and one or more $C_1+$ hydrocarbon, preferably $C_2$, forming a loaded second adsorption media and a gas stream comprising one or more $C_1+$ hydrocarbon, preferably a $C_1$ rich gas stream, 105. The second loaded adsorption media is regenerated and the adsorbed carbon dioxide and one or more $C_1+$ hydrocarbons, preferably $C_2$, are released 205 and the second adsorption media is regenerated from the loaded second adsorption media. The separated ($C_1$) hydrocarbons 229 can be recovered, used as fuel for a combustion process, flared, or a combination thereof. The released second treated carbon dioxide-rich gas stream comprising one or more $C_1+$ hydrocarbon, preferably $C_2$, 205 can be supplied to one or more additional separation unit for further treatment, recovered, reinjected into an injection well, or a combination thereof. Preferably, the adsorption process in the second separation unit is performed under reduced pressure.

Figure 3:
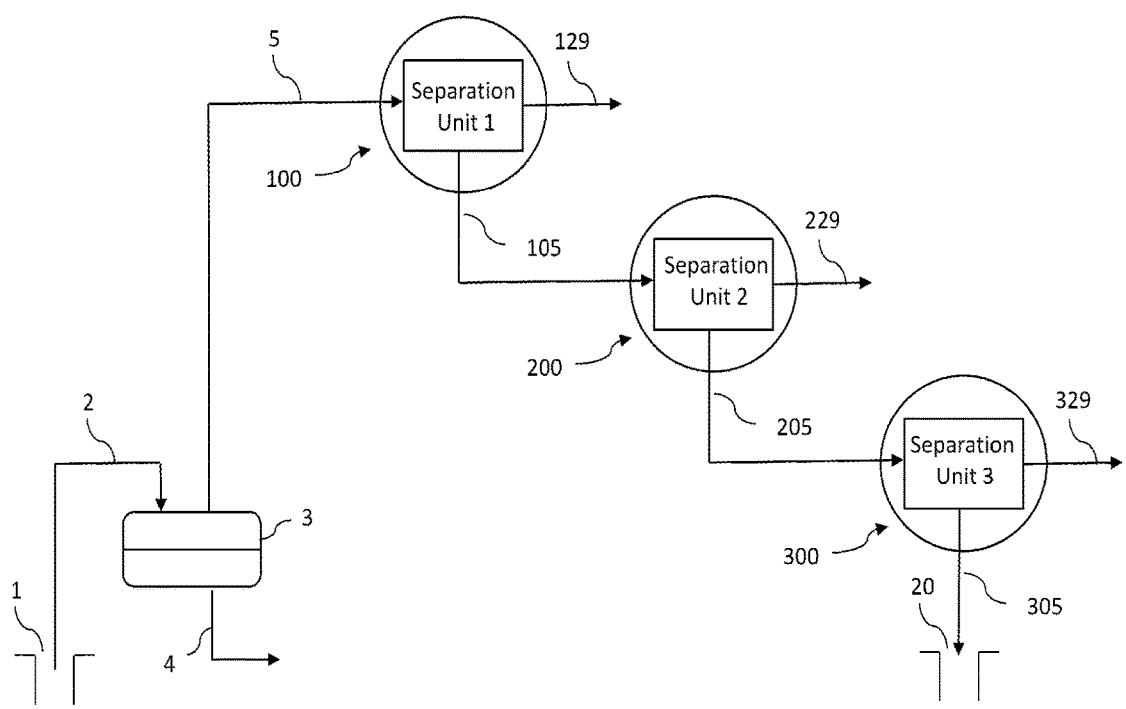
FIG. 3 is a schematic of a process of the present invention to sequentially remove $C_3+$, $C_1$, and $C_2$ from carbon dioxide feedstream produced from a production well.

Referring now to FIG. 3, a third embodiment of the process of the present invention is shown. The gas stream 5 from the separator 3 is passed through the first separation unit 100 containing the first adsorption media, preferably comprising a porous cross-linked polymeric adsorbent for the removal of one or more $C_1+$ hydrocarbons, preferably $C_3+$ hydrocarbons, 129 forming a first treated carbon dioxide-rich gas stream comprising one or more $C_1+$ hydrocarbon, preferably $C_1$ and $C_2$, 105. Said first treated carbon dioxide-rich gas stream 105 is then passed through a second separation unit 200 containing a second adsorption media 202, preferably comprising a pyrolized macroporous polymers adsorbent, wherein one or more $C_1+$ hydrocarbon, preferably $C_1$, 229 is separated from the adsorbed then regenerated second treated carbon dioxide-rich gas stream comprising one or more C$_1$+ hydrocarbon, preferably C$_2$ 205. Said second treated carbon dioxide-rich gas stream 205 is then passed through a third separation unit wherein C$_2$ 329 is separated from the carbon dioxide-rich gas stream 205 forming a third treated carbon dioxide-rich gas stream 305 which, may be supplied to one or more additional separation unit for further treatment, recovered, reinjected into an injection well 20 as shown in FIG. 3, or a combination thereof.

Figure 6:
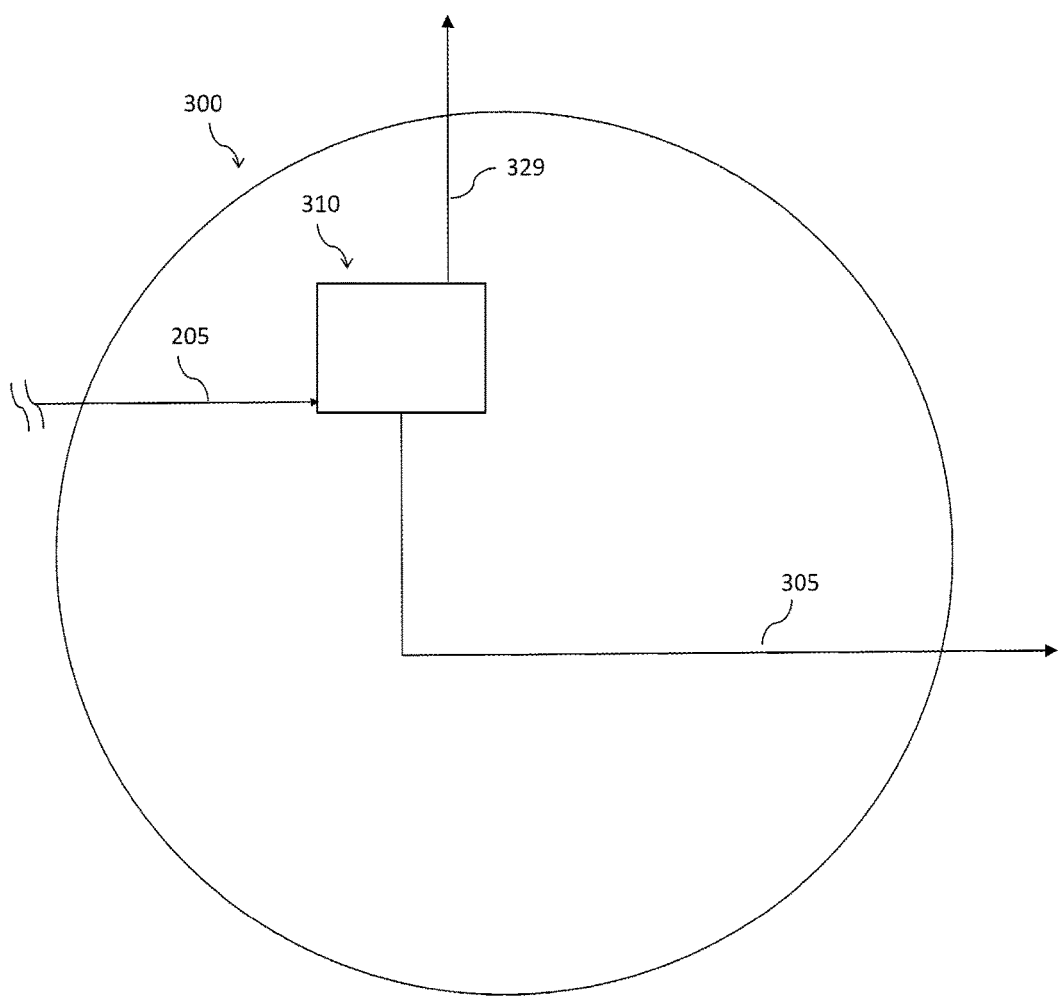
FIG. 6 is a schematic of a third separation unit of the present invention.

Referring to FIG. 6, preferably the third separation unit 310 comprises a chiller, a condenser, a dryer, a nitrogen removal media, a MEHRA process, or an amine scrubbing unit, for example using UCARSORB™ polymer adsorbent or SOLEXOL™ physical sorbents. Preferably the third separation unit 310 is a chiller or condenser and the one or more C$_1$+ hydrocarbon that is separated and liquefied is C$_2$.

The process of the present method comprises feeding a carbon dioxide gas feedstream, for example form a G/L effluent comprising gaseous and liquid hydrocarbons and carbon dioxide, into one or more separation unit, for example a first separation unit 100 as shown in FIG. 1, a first separation unit 100 and a second separation unit 200 as shown in FIG. 2, and a first separation unit 100, second separation unit 200, and a third separation unit 300 as shown in FIG. 3, wherein one or more hydrocarbon and/or contaminant is removed and recovered from each separation unit each separation step providing a treated carbon dioxide stream richer in carbon dioxide after the treatment than before. In a preferred embodiment of the preset invention, the process of the present invention comprises the use of three separation units (i.e., first, second, and third separation units) in a sequential and continuous manner.

In each separation unit the carbon dioxide, one or more C$_1$+ hydrocarbon gas, and/or contaminant is separated from the carbon dioxide-rich gas stream gas stream by adsorption into an adsorption media, selective to carbon dioxide, one or more hydrocarbon gas, and/or contaminant to be adsorbed, forming a loaded adsorbent media. The remaining gas stream passes out of the separation unit. The carbon dioxide, one or more hydrocarbon gas, and/or contaminant is recovered from the loaded adsorption media by regenerating the loaded adsorbent media which releases the adsorbed carbon dioxide, hydrocarbon gas, and/or contaminant forming adsorbent media that may be reused. The adsorption unit/regeneration unit of each separation unit is (1) independently the same unit wherein the adsorption/regeneration steps take place in the same unit, (2) distinct adsorption and regeneration units wherein the adsorption step take place in a separation unit and the regeneration step takes place in a regeneration unit which is not the separation unit, or (3) a mixture thereof.

In one embodiment of the method of the present invention, the means to regenerate the loaded adsorbent media and the regeneration step take place in the same unit or vessel where the adsorption occurs. In other words, the adsorption media is regenerated in place.

Figure 4:
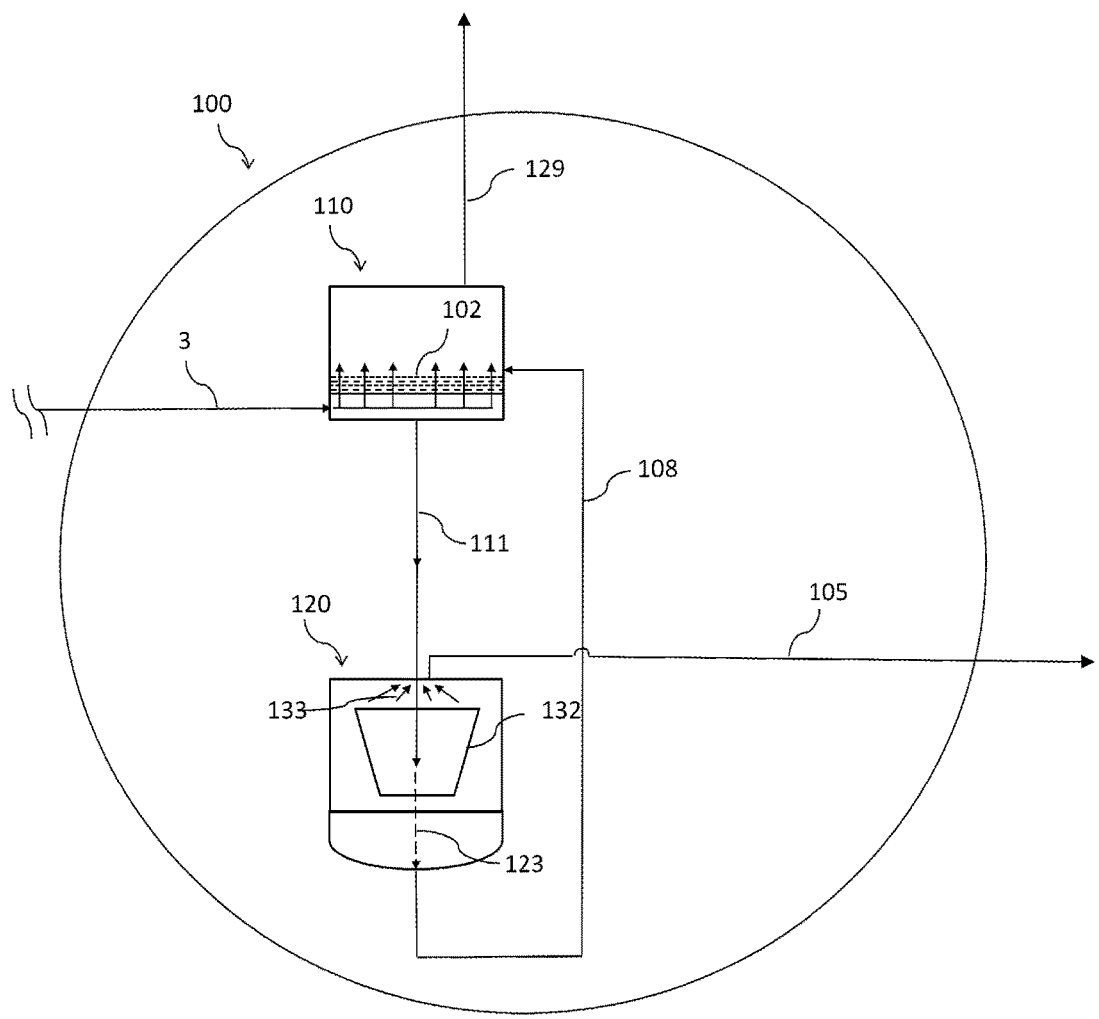
FIG. 4 is a schematic of a first adsorption/desorption unit of the present invention.
Figure 5:
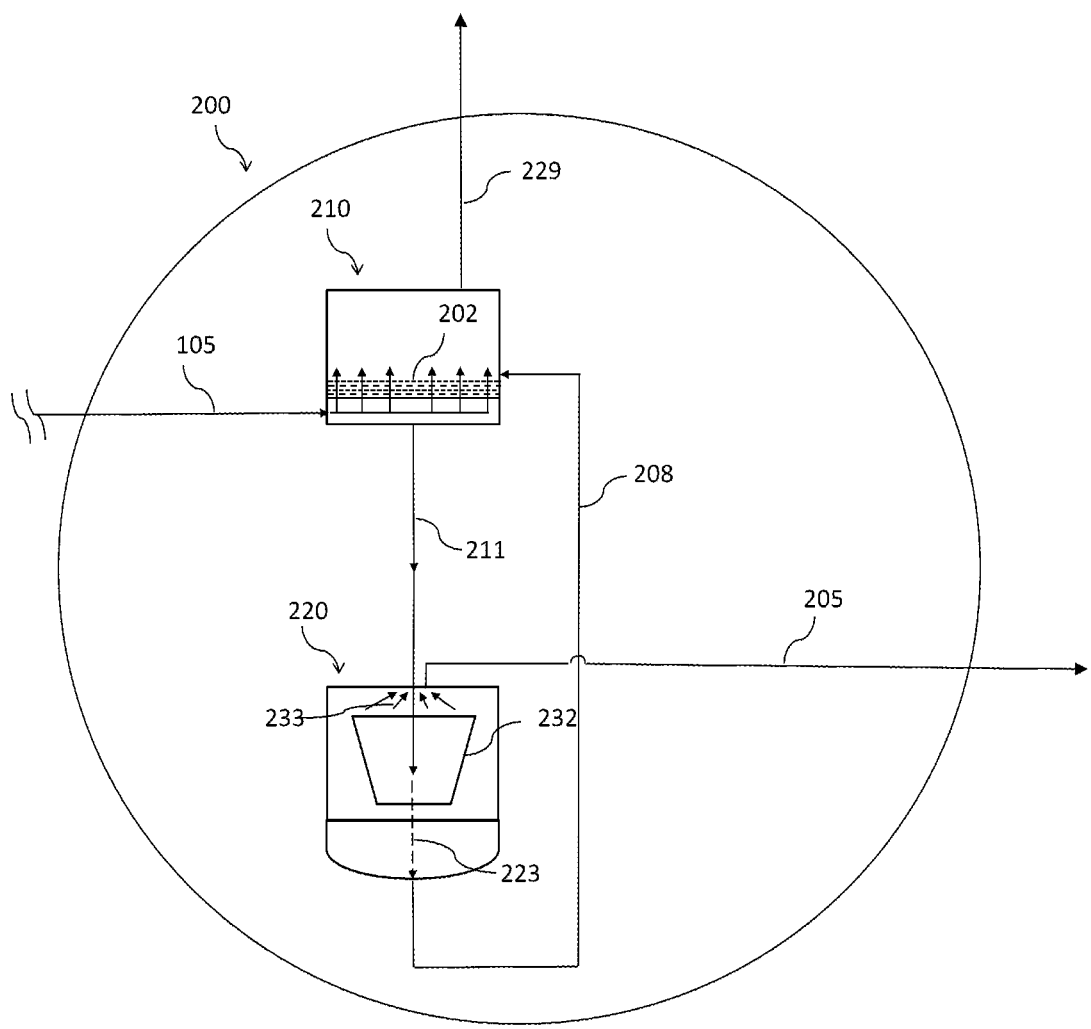
FIG. 5 is a schematic of a second adsorption/desorption unit of the present invention.

In another embodiment of the method of the present invention (FIGS. 4 and 5), the means to regenerate the loaded adsorbent media and the regeneration step takes place in a different unit or vessel than where the adsorption occurs. In other words, the adsorption media is transported to a regeneration unit, regenerated, and transported back to the adsorption unit. For example separation units, 100, and 200 each comprise an adsorption unit 110 and 210 comprising an adsorption bed 102 and 202 comprising an adsorbent media to form a loaded adsorbent media and a regeneration unit 120 and 220 comprising a means to regenerate 132 and 232 loaded adsorbent media causing the release of adsorbed hydrocarbons and/or other gases 133 and 233 from the loaded adsorbing media and forming regenerated adsorbent media which can be transported 108 and 208 back to the adsorption unit 110 and 210 for reuse.

In yet another embodiment of the method of the present invention, in one or more separation unit, the means to regenerate the loaded adsorbent media and the regeneration step take place in the same unit or vessel where the adsorption occurs and in one or more separation unit the means to regenerate the loaded adsorbent media and the regeneration step takes place in different units or vessels than where the adsorption occurs.

Suitable adsorbent media are solids having a microscopic structure. The internal surface of such adsorbents is preferably between 100 to 2000 m$^2$/g, more preferably between 500 to 1500 m$^2$/g, and even more preferably 1000 to 1300 m$^2$/g. The nature of the internal surface of the adsorbent in the adsorbent bed is such that C$_2$ and heavier hydrocarbons are adsorbed. Suitable adsorbent media include materials based on silica, silica gel, alumina or silica-alumina, zeolites, activated carbon, polymer supported silver chloride, copper-containing resins. Most preferred adsorbent media is a porous cross-linked polymeric adsorbent or a partially pyrolized macroporous polymer. Preferably, the internal surface of the adsorbent is non-polar.

In one embodiment, the present invention is the use of an adsorbent media to extract hydrocarbons from a carbon dioxide gas stream. The mechanism by which the macroporous polymeric adsorbent extracts the hydrocarbons from the carbon dioxide gas stream is a combination of adsorption and absorption; the dominating mechanism at least is believed to be adsorption. Accordingly, the terms "adsorption" and "adsorbent" are used throughout this specification, although this is done primarily for convenience. The invention is not considered to be limited to any particular mechanism.

When an adsorbent media has adsorbed any amount of C$_1$+ hydrocarbons it is referred to as "loaded". Loaded includes a range of adsorbance from a low level of hydrocarbons up to and including saturation with adsorbed hydrocarbons.

The term "macroporous" is used in the art interchangeably with "macroreticular," and refers in general to pores with diameters of about 500 Å or greater. "Mesopores" are characterized as pores of between 50 Å and larger but less than 500 Å. "Micropores" are characterized as pores of less than 50 Å. The engineered distribution of these types of pores gives rise to the desired properties of high adsorption capacity for hydrocarbons and ease of desorption of hydrocarbons under convenient/practical chemical engineering process modifications (increase in temperature or reduced pressure [vacuum]). The process giving rise to the distribution of micropores, mesopores and macropores can be achieved in various ways, including forming the polymer in the presence of an inert diluent or other porogen to cause phase separation and formation of micropores by post cross-linking.

In one embodiment, the adsorbent media of the present invention is a macroporous polymeric adsorbent of the present invention is a post cross-linked polymeric synthetic adsorbents engineered to have high surface area, high pore volume and high adsorption capacities as well as an engineered distribution of macropores, mesopores and micropores.

Preferably, the macroporous polymeric adsorbent of the present invention is hypercrosslinked and/or methylene bridged having the following characteristics: a BET surface area of equal to or greater than 500 m$^2$/g and preferably equal to or greater than 1,000 m$^2$/g, and having a particle size of 300 microns to 1500 microns, preferably 500 to 1200 microns. Examples of monomers that can be polymerized to form macroporous polymeric adsorbents useful are styrene, alkylstyrenes, halostyrenes, haloalkylstyrenes, vinylphenols, vinylbenzyl alcohols, vinylbenzyl halides, and vinylnaphthalenes. Included among the substituted styrenes are ortho-, meta-, and para-substituted compounds. Specific examples are styrene, vinyltoluene, ethylstyrene, t-butylstyrene, and vinyl benzyl chloride, including ortho-, meta-, and para-isomers of any such monomer whose molecular structure permits this type of isomerization. Further examples of monomers are polyfunctional compounds. One preferred class is polyvinylidene compounds, examples of which are divinylbenzene, trivinylbenzene, ethylene glycol dimethacrylate, divinylsulfide and divinylpyridine. Preferred polyvinylidene compounds are di- and trivinyl aromatic compounds. Polyfunctional compounds can also be used as crosslinkers for the monomers of the first group.

One preferred method of preparing the polymeric adsorbent is by swelling the polymer with a swelling agent, then crosslinking the polymer in the swollen state, either as the sole crosslinking reaction or as in addition to crosslinking performed prior to swelling. When a swelling agent is used, any pre-swelling crosslinking reaction will be performed with sufficient crosslinker to cause the polymer to swell when contacted with the swelling agent rather than to dissolve in the agent. The degree of crosslinking, regardless of the stage at which it is performed, will also affect the porosity of the polymer, and can be varied to achieve a particular porosity. Given these variations, the proportion of crosslinker can vary widely, and the invention is not restricted to particular ranges. Accordingly, the crosslinker can range from about 0.25% of the polymer to about 45%. Best results are generally obtained with about 0.75% to about 8% crosslinker relative to the polymer, the remaining (noncrosslinking) monomer constituting from about 92% to about 99.25% (all percentages are by weight).

Other macroporous polymeric adsorbents useful in the practice of this invention are copolymers of one or more monoaromatic monomers with one or more nonaromatic monovinylidene monomers. Examples of the latter are methyl acrylate, methyl methacrylate and methylethyl acrylate. When present, these nonaromatic monomers preferably constitute less than about 30% by weight of the copolymer.

The macroporous polymeric adsorbent is prepared by conventional techniques, examples of which are disclosed in various United States patents. Examples are U.S. Pat. Nos. 4,297,220; 4,382,124; 4,564,644; 5,079,274; 5,288,307; 4,950,332; and 4,965,083. The disclosures of each of these patents are incorporated herein by reference in their entirety.

For polymers that are swollen and then crosslinked in the swollen state, the crosslinking subsequent to swelling can be achieved in a variety of ways, which are further disclosed in the patents cited above. One method is to first haloalkylate the polymer, and then swell it and crosslink by reacting the haloalkyl moieties with aromatic groups on neighboring chains to form an alkyl bridge. Haloalkylation is achieved by conventional means, an example of which is to first swell the polymer under non-reactive conditions with the haloalkylating agent while including a Friedel-Crafts catalyst dissolved in the haloalkylating agent. Once the polymer is swollen, the temperature is raised to a reactive level and maintained until the desired degree of haloalkylation has occurred. Examples of haloalkylating agents are chloromethyl methyl ether, bromomethyl methyl ether, and a mixture of formaldehyde and hydrochloric acid. After haloalkylation, the polymer is swelled further by contact with an inert swelling agent. Examples are dichloroethane, chlorobenzene, dichlorobenzene, ethylene dichloride, methylene chloride, propylene dichloride, and nitrobenzene. A Friedel-Crafts catalyst can be dissolved in the swelling agent as well, since the catalyst will be used in the subsequent crosslinking reaction. The temperature is then raised to a level ranging from about 60° C. to about 85° C. in the presence of the catalyst, and the bridging reaction proceeds. Once the bridging reaction is complete, the swelling agent is removed by solvent extraction, washing, drying, or a combination of these procedures.

The pore size distribution and related properties of the finished adsorbent can vary widely and no particular ranges are critical to the invention. In most applications, best results will be obtained at a porosity (total pore volume) within the range of from 0.5 to 1.5 cc/g of the polymer. A preferred range is 0.7 to 1.3 cc/g. Within these ranges, the amount contributed by macropores (i.e., pores having diameters of 500 Å or greater) will preferably range from 0.025 to 0.6 cc/g, and most preferably from 0.04 to 0.5 cc/g. The surface area of the polymer, as measured by nitrogen adsorption methods such as the well-known BET method, will in most applications be within the range of 150 to 2100 m$^2$/g, and preferably from 400 to 1400 m$^2$/g. The average pore diameter will most often range from 10 Å to about 100 Å.

The form of the macroporous polymeric adsorbent is likewise not critical and can be any form which is capable of containment and contact with a flowing compressed air stream. Granular particles and beads are preferred, ranging in size from about 50 to about 5,000 microns, with a range of about 500 to about 3,000 microns particularly preferred. Contact with the adsorbent can be achieved by conventional flow configurations of the gas, such as those typically used in fluidized beds or packed beds. The adsorbent can also be enclosed in a cartridge for easy removal and replacement and a more controlled gas flow path such as radial flow.

The macroporous polymeric adsorbent can function effectively under a wide range of operating conditions. The temperature will preferably be within any range which does not cause further condensation of vapors or any change in physical or chemical form of the adsorbent. Preferred operating temperatures are within the range of from 5° C. to 75° C., and most preferably from 10° C. to 50° C. In general, operation at ambient temperature or between ambient temperature and 10° C. to 15° C. above ambient will provide satisfactory results. The pressure of the carbon dioxide gas stream entering the adsorbent bed can vary widely as well, preferably extending from 2 psig (115 kPa) to 1000 psig (7000 kPa). The pressure will generally be dictated by the plant unit where the product gas will be used. A typical pressure range is from 100 psig (795 kPa) to 300 psig (2170 kPa). The residence time of the hydrocarbons stream in the adsorbent bed will most often range from 0.02 second to 5 seconds, and preferably from 0.3 second to 3.0 seconds. The space velocity of the hydrocarbons stream through the bed will most often fall within the range of 0.1 foot per second to 5 feet per second, with a range of 0.3 foot per second to 3 feet per second preferred. Finally, the relative humidity can have any value up to 100%, although for convenience, the preferred range of relative humidity is about 25% to about 98%.

The macroporous polymeric adsorbents of the present invention described herein above can be used to separate ethane, propane, butane, pentane, and heaver hydrocarbons from mixed gases containing methane. Preferably, the macroporous polymeric adsorbents of the present invention adsorb equal to or greater than 60 cm$^3$ STP of propane per gram of sorbent at 35° C. and 500 mmHg of propane. Preferably, the adsorbents of the present invention adsorb equal to or greater than 60 cm$^3$ STP of n-butane per gram of sorbent at 35° C. and 100 mmHg of n-butane. Furthermore, these materials are able to be degassed of propane or n-butane and then able to readsorb equal to or greater than 60 cm$^3$ STP of propane per gram of sorbent at 35° C. and 500 mmHg of propane or readsorb greater than 60 cm$^3$ STP of n-butane per gram of sorbent at 35° C. and 100 mmHg of n-butane at least once. Preferably, the adsorbents of the present invention adsorb equal to or greater than 30 cm$^3$ STP of ethane per gram of sorbent at 35° C. and 600 mmHg of ethane. Preferably, the adsorbents of the present invention adsorb equal to or greater than 100 cm$^3$ STP of pentane per gram of sorbent at 35° C. and 50 mmHg of pentane.

In another embodiment, the adsorbent media of the present invention is a pyrolized macroporous polymeric adsorbent media to extract hydrocarbons from a hydrocarbons stream.

Pyrolized macroporous polymeric adsorbent media are well known, for instance see U.S. Pat. No. 4,040,990, incorporated by reference herein in its entirety. Partially pyrolyzed particles, preferably in the form of beads or spheres, produced by the controlled decomposition of a synthetic polymer of specific initial porosity. In a preferred embodiment, the pyrolyzed particles are derived from the thermal decomposition of macroreticular ion exchange resins containing a macroporous structure.

In general pyrolysis comprises subjecting the starting polymer to controlled temperatures for controlled periods of time under certain ambient conditions. The primary purpose of pyrolysis is thermal degradation while efficiently removing the volatile products produced.

The maximum temperatures may range from about 300° C. to up to about 900° C., depending on the polymer to be treated and the desired composition of the final pyrolyzed particles. Higher temperature, e.g., about 700° C. and higher result in extensive degradation of the polymer with the formation of molecular sieve sized pores in the product.

Most desirably, thermal decomposition (alternatively denoted "pyrolysis" or "heat treatment") is conducted in an inert atmosphere comprised of, for example, argon, neon, helium, nitrogen, or the like, using beads of macroreticular synthetic polymer substituted with a carbon-fixing moiety which permits the polymer to char without fusing in order to retain the macroreticular structure and give a high yield of carbon. Among the suitable carbon-fixing moieties are sulfonate, carboxyl, amine, halogen, oxygen, sulfonate salts, carboxylate salts and quaternary amine salts. These groups are introduced into the starting polymer by well-known conventional techniques, such as those reactions used to functionalize polymers for production of ion exchange resins. Carbon-fixing moieties may also be produced by imbibing a reactive precursor thereof into the pores of macroreticular polymer which thereupon, or during heating, chemically binds carbon-fixing moieties onto the polymer. Examples of these latter reactive precursors include sulfuric acid, oxidizing agents, nitric acid, Lewis acids, acrylic acid, and the like.

Suitable temperatures for practicing the process of this invention are generally within the range of 300° C. to about 900° C., although higher temperatures may be suitable depending upon the polymer to be treated and the desired composition of the final pyrolyzed product. At temperatures above about 700° C. the starting polymer degrades extensively with the formation of molecular sieve sized pores in the product, i.e., 4 Å to 6 Å average critical dimension, yielding a preferred class of adsorbents according to this invention. At lower temperatures, the thermally-formed pores usually range from 6 Å to as high as 50 Å in average critical size. A preferred range of pyrolysis temperatures is between about 400° C. and 800° C. As will be explained more fully hereinafter, temperature control is essential to yield a partially pyrolyzed material having the composition, surface area, pore structures and other physical characteristics of the desired product. The duration of thermal treatment is relatively unimportant, providing a minimum exposure time to the elevated temperature is allowed.

A wide range of pyrolyzed resins may be produced by varying the porosity and/or chemical composition of the starting polymer and also by varying the conditions of thermal decomposition. In general, the pyrolyzed resins of the invention have a carbon to hydrogen ratio of 1.5:1 to 20:1, preferably 2.0:1 to 10:1, whereas activated carbon normally has a C/H ratio much higher, at least greater than 30:1 (Carbon and Graphite Handbook, Charles L. Mantell, Interscience Publishers, N.Y. 1968, p. 198). The product particles contain at least 85% by weight of carbon with the remainder being principally hydrogen, alkali metals, alkaline earth metals, nitrogen, oxygen, sulfur, chlorine, etc., derived from the polymer or the functional group (carbon-fixing moiety) contained thereon and hydrogen, oxygen, sulfur, nitrogen, alkali metals, transition metals, alkaline earth metals and other elements introduced into the polymer pores as components of a filler (may serve as a catalyst and/or carbon-fixing moiety or have some other functional purpose).

The pore structure of the final product must contain at least two distinct sets of pores of differing average size, i.e., multimodal pore distribution. The larger pores originate from the macroporous resinous starting material which preferably contains macropores ranging from between 50 Å to 100,000 Å in average critical dimension. The smaller pores, as mentioned previously, generally range in size from about 4 to about 50 Å, depending largely upon the maximum temperature during pyrolysis. Such multimodal pore distribution is considered a novel and essential characteristic of the composition of the invention.

The pyrolyzed polymers of the invention have relatively large surface area resulting from the macroporosity of the starting material and the smaller pores developed during pyrolysis. In general the overall surface area as measured by nitrogen adsorption ranges between about 50 and 1500 m$^2$/gram. Of this, the macropores will normally contribute 6 to 700 m$^2$/gram, preferably 6 to 200 m$^2$/g, as calculated by mercury intrusion techniques, with the remainder contributed by the thermal treatment. Pore-free polymers, such as "gel" type resins which have been subjected to thermal treatment in the prior art do not contribute the large pores essential to the adsorbents of the invention nor do they perform with the efficiency of the pyrolyzed polymers described herein.

The duration of pyrolysis depends upon the time needed to remove the volatiles from the particular polymer and the heat transfer characteristics of the method selected. In general, the pyrolysis is very rapid when the heat transfer is rapid, e.g., in an oven where a shallow bed of material is pyrolyzed, or in a fluidized bed. To prevent burning of the pyrolyzed polymer, normally the temperature of the polymer is reduced to not more than 400° C., preferably not more than 300° C., before the pyrolyzed material is exposed to air.

The most desirable method of operation involves rapid heating to the maximum temperature, holding the temperature at the maximum for a short period of time (in the order of 0 to 20 minutes) and thereafter quickly reducing the temperature to room temperature before exposing the sample to air. Products according to the invention have been produced by this preferred method by heating to 800° C. and cooling in a period of 20 to 30 minutes. Longer holding periods at the elevated temperatures are also satisfactory, since no additional decomposition appears to occur unless the temperature is increased.

Activating gases such as $CO_2$, $NH_3$, $O_2$, $H_2O$ or combinations thereof in small amounts tend to react with the polymer during pyrolysis and thereby increase the surface area of the final material. Such gases are optional and may be used to obtain special characteristics of the adsorbents.

The starting polymers which may be used to produce the pyrolyzed resins of the invention include macroreticular homopolymers or copolymers of one or more monoethylenically or polyethylenically unsaturated monomers or monomers which may be reacted by condensation to yield macroreticular polymers and copolymers. The macroreticular resins used as precursors in the formation of macroreticular heat treated polymers are not claimed as new compositions of matter in themselves. Any of the known materials of this type with an appropriate carbon-fixing moiety is suitable. The preferred monomers are those aliphatic and aromatic materials which are ethylenically unsaturated.

Examples of suitable monoethylenically unsaturated monomers that may be used in making the granular macroreticular resin include: esters of acrylic and methacrylic acid such as methyl, ethyl, 2-chloroethyl, propyl, isobutyl, isopropyl, butyl, tert-butyl, sec-butyl, ethylhexyl, amyl, hexyl, octyl, decyl, dodecyl, cyclohexyl, isobornyl, benzyl, phenyl, alkylphenyl, ethoxymethyl, ethoxyethyl, ethoxypropyl, propoxymethyl, propoxyethyl, propoxypropyl, ethoxyphenyl, ethoxybenzyl, ethoxycyclohexul, hydroxyethyl, hydroxypropyl, ethylene, propylene, isobutylene, diisobutylene, styrene, ethylvinylbenzene, vinyltoluene, vinylbenzylchloride, vinyl chloride, vinyl acetate, vinylidene chloride, dicyclopentadiene, acrylonitrile, methacrylonitrile, acrylamide, methacrylamide, diacetone acrylamide, functional monomers such as vinylbenzene, sulfonic acid, vinyl esters, including vinyl acetate, vinyl propionate, vinyl butyrate, vinyl laurate, vinyl ketones including vinyl methyl ketone, vinyl ethyl ketone, vinyl isopropyl ketone, vinyl n-butyl ketone, vinyl hexyl ketone, vinyl octyl ketone, methyl isopropenyl ketone, vinyl aldehydes including acrolein, methacrolein, crotonaldehyde, vinyl ethers including vinyl methyl ether, vinyl ethyl ether, vinyl propyl ether, vinyl isobutyl ether, vinylidene compounds including vinylidene chloride bromide, or bromochloride, also the corresponding neutral or half-acid half-esters or free diacids of the unsaturated dicarboxylic acids including itaconic, citraconic, aconitic, fumaric, and maleic acids, substituted acrylamides, such as N-monoalkyl, —N,N-dialkyl-, and N-dialkylaminoalkylacrylamides or methacrylamides where the alkyl groups may have from one to eighteen carbon atoms, such as methyl, ethyl, isopropyl, butyl, hexyl, cyclohexyl, octyl, dodecyl, hexadecyl and octadecyl aminoalkyl esters of acrylic or methacrylic acid, such as .beta.-dimethylaminoethyl, .beta.-diethylaminoethyl or 6-dimethylaminohexyl acrylates and methacrylates, alkylthioethyl methacrylates and acrylates such as ethylthioethyl methacrylate, vinylpyridines, such as 2-vinylpyridine, 4-vinylpyridine, 2-methyl-5-vinylpyridine, and so on. In the case of copolymers containing ethylthioethyl methacrylate, the products can be oxidized to, if desired, the corresponding sulfoxide or sulfone.

Polyethylenically unsaturated monomers which ordinarily act as though they have only one such unsaturated group, such as isoprene, butadiene, and chloroprene, may be used as part of the monoethylenically unsaturated category.

Examples of polyethylenically unsaturated compounds include: divinylbenzene, divinylpyridine, divinylnaphthalenes, diallyl phthalate, ethylene glycol diacrylate, ethylene glycol dimethacrylate, trimethylolpropanetrimethacrylate, divinylsulfone, polyvinyl or polyallyl ethers of glycol, of glycerol, of pentaerythritol, of diethyleneglycol, of monothio or dithio-derivatives of glycols, and of resorcinol, divinylketone, divinylsylfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, N,N'-methylenediacrylamide, N,N'-methylenedimethacrylamide, N,N'-ethylenediacrylamide, trivinylbenzene, trivinylnaphthalenes, and polyvinylanthracenes.

A preferred class of monomers of this type is aromatic ethylenically unsaturated molecules such as styrene, vinyl pyridine, vinyl naphthalene, vinyl toluene, phenyl acrylate, vinyl xylenes, and ethylvinylbenzene.

Examples of preferred polyethylenically unsaturated compounds include divinyl pyridine, divinyl naphthalene, divinylbenzene, trivinylbenzene, alkyldivinylbenzenes having from 1 to 4 alkyl groups of 1 to 2 carbon atoms substituted in the benzene nucleus, and alkyltrivinylbenzenes having 1 to 3 alkyl groups of 1 to 2 carbon atoms substituted in the benzene nucleus. Besides the homopolymers and copolymers of these poly(vinyl) benzene monomers, one or more of them may be copolymerized with up to 98% (by weight of the total monomer mixture) of (1) monoethylenically unsaturated monomers, or (2) polyethylenically unsaturated monomers other than the poly(vinyl) benzenes just defined, or (3) a mixture of (1) and (2). Examples of the alkyl-substituted di- and tri-vinyl-benzenes are the various vinyltoluenes, the divinylethylbenzene, 1,4-divinyl-2,3,5,6-tetramethylbenzene, 1,3,5-trivinyl-2,4,6-trimethylbenzene, 1,4-divinyl, 2,3,6-triethylbenzene, 1,2,4-trivinyl-3,5-diethylbenzene, 1,3,5-trivinyl-2-methylbenzene.

Most preferred are copolymers of styrene, divinylbenzene, and ethylvinylbenzene.

Examples of suitable condensation monomers include: (a) aliphatic dibasic acids such as maleic acid, fumaric acid, itaconic acid, 1,1-cyclobutanedicarboxylic acid, etc.; (b) aliphatic diamines such as piperazine, 2-methylpiperazine, cis, cis-bis (4-aminocyclohexyl) methane, metaxylylenediamine, etc.; (c) glycols such as diethylene glycol, triethylene glycol, 1,2-butanediol, neopentyl glycol etc.; (d) bischloroformates such as cis and trans-1,4-cyclohexyl bischloroformate, 2,2,2,4-tetramethyl-1,3-cyclobutyl bischloroformate and bischloroformates of other glycols mentioned above, etc.; (e) hydroxy acids such as salicylic acid, m- and p-hydroxy-benzoic acid and lactones, derived therefrom such as the propiolactones, valerolactones, caprolactones, etc.; (f) diisocyanates such as cis and trans-cyclopropane-1,2-diisocyanate, cis and trans-cyclobutane-1-2-diisocyanate etc.; (g) aromatic diacids and their derivatives (the esters, anhydrides and acid chlorides) such as phthalic acid, phthalic anhydride, terephthalic acid, isophthalic acid, dimethylphthalate, etc.; (h) aromatic diamines such as benzidine, 4,4'-methylenediamine, bis(4-aminophenyl) ether, etc.;

(i) bisphenols such as bisphenol A, bisphenol C, bisphenol F, phenolphthalein, recorcinol, etc.; (j) bisphenol bis(chloroformates) such as bisphenol A bis(chloroformate), 4,4'-dihydroxybenzophenone bis(chloroformate) etc.; (k) carbonyl and thiocarbonyl compounds such as formaldehyde, acetaldehyde, thioacetone acetone, etc.; (l) phenol and derivatives such as phenol, alkylphenols, etc.; (m) polyfunctional cross-linking agents such as tri or poly basic acids such as trimellitic acid, tri or polyols such as glycerol, tri or polyamines such as diethylenetriamine; and other condensation monomers and mixtures of the foregoing.

Ion exchange resins produced from aromatic and/or aliphatic monomers provide a preferred class of starting polymers for production of porous adsorbents. The ion exchange resin may also contain a functional group selected from cation, anion, strong base, weak base, sulfonic acid, carboxylic acid, oxygen containing, halogen and mixtures of the same. Further, such ion exchange resins may optionally contain an oxidizing agent, a reactive substance, sulfuric acid, nitric acid, acrylic acid, or the like at least partially filling the macropores of the polymer before heat treatment.

The synthetic polymer may be impregnated with a filler such as carbon black, charcoal, bonechar, sawdust or other carbonaceous material prior to pyrolysis. Such fillers provide an economical source of carbon which may be added in amounts up to about 90% by weight of the polymer.

The starting polymers, when ion exchange resins, may optionally contain a variety of metals in their atomically dispersed form at the ionic sites. These metals may include iron, copper, silver, nickel, manganese, palladium, cobalt, titanium, zirconium, sodium, potassium, calcium, zinc, cadmium, ruthenium, uranium and rare earths such as lanthanum. By utilizing the ion exchange mechanism it is possible for the skilled technician to control the amount of metal that is to be incorporated as well as the distribution.

Although the incorporation of metals onto the resins is primarily to aid their ability to serve as catalytic agents, useful adsorbents may also contain metal.

Synthetic polymers, ion exchange resins whether in the acid, base or metal salt form are commercially available. According to the invention there is also provided an adsorption process for separating components from a gaseous or liquid medium which comprises contacting the medium with particles of a pyrolyzed synthetic polymer.

For example it has been discovered that a styrenedivinylbenzene based strongly acidic exchange resin pyrolyzed from any of the forms of Hydrogen, Iron (III), Copper(II), Silver (I) or Calcium (II) can decrease the concentration of vinylchloride in air preferably dry air from initial concentration of 2 ppm to 300,000 ppm to a level of less than 1 ppm at flow rates of 1 bedvolume/hour to 600 bedvolume/min. preferably 10 to 200 bedvolume/minute.

The partially pyrolyzed macroporous polymer adsorbent of the present invention disclosed herein above are able to adsorb greater than 25 $cm^3$ STP of ethane per gram of sorbent at 35° C. and 200 mmHg of ethane and greater than 30 $cm^3$ STP of propane per gram of sorbent at 35° C. and 100 mmHg of propane. Furthermore, these materials are able to be degassed of ethane or propane and then able to readsorb greater than 25 $cm^3$ STP of ethane per gram of sorbent at 35° C. and 200 mmHg of ethane, or readsorb greater than 30 $cm^3$ STP of propane per gram of sorbent at 35° C. and 100 mmHg of propane one or more times.

The separation process comprises passing a hydrocarbons stream through an adsorber bed charged with the adsorbent (s) of the invention. Preferably, the ethane and/or propane and/or butane and/or pentane and/or heavier hydrocarbons, which are selectively adsorbed, can be readily desorbed either by lowering the pressure or by increasing the temperature of the adsorber bed resulting in a regenerated adsorbent. The adsorbent so regenerated can be reused as an adsorbent for the separation of ethane and/or propane and/or butane and/or pentane and/or heavier hydrocarbons from the hydrocarbons stream.

The adsorption media in the adsorption beds of the one or more separation units may be the same or different than the adsorption media of any of the other adsorption beds. For example, the adsorption media of the adsorption bed 102 of the first separation unit 100 may be the same or different than the adsorption media of the adsorption bed 202 of the second separation unit 200. Furthermore, the adsorbent in each bed may comprise one or more adsorbent, the mixture may be a homogeneous mixture throughout the bed, a layered bed in a batch process, or the like. For example, the adsorption media of each adsorption bed 102 and/or 202 may be a mixture of two or more adsorbent media.

The flow rate of each inlet gas into a separation unit may be the same or different from the flow rates of the inlet gases to the other separation units. For example, each flow rate of the inlet gas 5, 105, or optionally 205, i.e., a first flow rate, a second flow rate, and a third flow rate, respectively, to each separation unit 100, 200, and 300, respectively, is independent from one another. In one embodiment, the flow rate of all inlet gases 5, 105, and optionally 205 are the same, i.e., 5 is the same as 105 is the same as 205. In another embodiment, the flow rate of all inlet gases 5, 105, and optionally 205 are different from each other, i.e., 5 is different from 105 which is different from 205. In yet another embodiment of the present invention, two of the inlet gases 5, 105, and optionally 205 are the same and the other is different, for example 5 is the same as 105 but different from 205 or 5 is the same as 205 but different from 105 or 105 is the same as 205 but different from 5. For each separation unit, the flow rate is proportional to the bed saturation pressure for the component being removed. The flow rate in different separation units may be relative to one another; for example, one may be used as a reference and the others are any factor between 1 and 1000 times (×) larger, e.g., 1.25×, 1.5×, 1.75×, 2×, 3×, 4×, 5×, etc., or any fraction between 1 and 0.001 times (×) smaller, e.g., 0.9×, 0.75×, 0.5×, 0.25×, 0.1×, 0.05×, 0.001× and the like, or a combination of one larger and one smaller.

For example, a porous crosslinked polymer adsorbent can remove propane, butane, and pentane from mixtures with hydrocarbons. Furthermore, when the system is operated appropriately, the porous crosslinked polymer adsorbent can remove pentane from mixtures with butane and propane, or butane from mixtures with propane. This can be accomplished by controlling the time the sorbent is exposed to the mixed gas, e.g., flow rate of the inlet gas. In this case the more condensable component will be adsorbed at a higher purity than the less condensable component as the exposure time is lengthened. Another example is a porous pyrolized polymeric adsorbent media can be used to remove ethane from mixtures with methane. The mixed gas stream that leaves the separation unit is then transferred to further separation unit.

In another embodiment of the present invention, after sequential removal of one or more hydrocarbons from the carbon dioxide gas stream the resulting carbon dioxide-rich gas stream may further be treated to remove other contaminants such as acid gases, for example $H_2S$, $SO_2$, $CS_2$, COS, HCN, $NH_3$, mercaptans, and the like; other gases, for example $O_2$, $N_2$, and the like; and water by passing the carbon dioxide rich gas stream through one or more contaminant separation unit. Any suitable adsorbent, such as those listed herein above, may be employed to remove the desired contaminant. The contaminant(s) may be recovered, treated, vented, or combination thereof.

Each separation unit may comprise an adsorption unit and a regeneration unit. For illustrative purpose, separation unit 100 and 200 comprises an adsorption unit 110 and 210 and a regeneration unit 120 and 220. The following description with regard to components and unit steps uses the separation unit 100 depicted in FIG. 4 for reference, but applies as well to the separation units 200. The separation process comprises the steps of (a) passing a hydrocarbons feedstream 5 through an adsorption unit 110 comprising an adsorbent bed 102 comprising an adsorbent media which adsorbs one or more $C_1+$ hydrocarbon ($C_1$, $C_2$, $C_3$, $C_4$, $C_5$, etc.) to obtain a treated carbon dioxide-rich gas product 105, (b) transporting 111 adsorbent loaded with one or more hydrocarbons from the adsorption unit 110 to a regeneration unit 120 comprising a means 132 to regenerate the loaded adsorbent media whereby by causing the release of the one or more hydrocarbons 133 from the loaded adsorbing media and forming regenerated adsorbent media 123, (c) wherein the regenerated adsorbent media 123 is transported 108 back to the adsorption unit 110 for reuse, and (d) the released one or more hydrocarbons 133 are discharged 129, (e.g., recovered, excluded, by-passed, liquefied, or flared) individually or as a mixture of gases (e.g., as $C_1$, $C_2$, $C_3$, $C_4$, $C_5$, etc.).

For each separation unit comprising an adsorption unit and a regeneration unit, the adsorption step and/or regeneration step of the process of the present invention may operate in a batch process, a semi-continuous process, a continuous process, or combination thereof. For instance in one embodiment of the present invention, both the adsorption step and the regeneration step of a separation unit may operate in the batch mode. In another embodiment of the present invention both the adsorption step and the regeneration step of a separation unit may operate in the semi-continuous mode. In yet another embodiment of the present invention both the adsorption step and the regeneration step of a separation unit may operate in the continuous mode. Each of the two or three separation units may have the same or different modes of operation as the others.

Alternatively, in one embodiment of the present invention, for each separation unit comprising an adsorption unit and a regeneration unit, the adsorption step may operate in a batch, semi-continuous, or continuous mode while the regeneration step operates in a different mode than that of the adsorption step. For example, in one embodiment of the present invention the adsorption step may operate in a batch mode while the regeneration step operates in a continuous mode. In another embodiment of the present invention the adsorption step may operate in a continuous mode while the regeneration step operates in a continuous mode. All possible combinations of batch, semi-continuous, and continuous modes for the adsorbent step and regeneration step are considered within the scope of the present invention. Each of the two or three or more separation units may have the same or different modes of operation as the others.

Adsorption is in many situations a reversible process. The practice of removing volatiles from an adsorption media can be accomplished by reducing the pressure over the media, heating, or the combination of reduced pressure and heating. In either case the desired outcome is to re-volatilize the trapped vapors, and subsequently remove them from the adsorbent so that it can be reused to capture additional volatiles. Preferably, the adsorption media of the present invention when regenerated, desorbs adsorbed gases in an amount equal to or greater than 75 percent of the amount adsorbed, more preferably equal to or greater than 85 percent, more preferably equal to or greater than 90 percent, more preferably equal to or greater than 95 percent, more preferably equal to or greater than 99 percent and most preferably virtually all the hydrocarbons adsorbed.

Traditional means of heating adsorbent media for the purpose of removing adsorbed volatiles that utilize conventional heating systems such as heated gas (air or inert gas), or radiant heat contact exchangers are suitable for use in the present NGL separation process as part of the adsorbent media regeneration step.

Preferably, the hydrocarbons stream passed through the adsorbent bed of one or more of the separation unit is performed in a pressure swing adsorption (PSA) vessel containing said adsorbent media, a temperature swing adsorption (TSA) vessel containing said adsorbent media, or a PSA vessel in combination with a TSA vessel.

Alternatively, one or more of the separation unit of the present invention employs a regeneration unit using a microwave heating system as part of the adsorbent media regeneration step. Such a microwave heating system provides a heating system and method for removing volatiles from adsorbent media with higher thermal efficiency at a reduced cost. For example, referring to FIG. 4, a separation unit 100 may comprise a regeneration unit 120 wherein the heating system 132 is a microwave heating system. The operating temperatures of the microwave heating system 132 can range from 105 to 350° C., preferably from 140 to 250° C., and more preferably from 145 to 200° C. Pressures of from 20 to 600 psia, preferably 100 to 400 psia, and more preferably 150 to 200 psia can be used. A microwave power source 130 (not shown in FIG. 4) heats the adsorbent media in the microwave heating system 132 causing the hydrocarbons to vaporize 133.

The microwave heating system 132 can irradiate a loaded adsorbent media to desorb volatile materials. Irradiation of adsorbent media with microwave radiation can provide an economical and thermally efficient alternative for heating adsorbent materials to remove adsorbed volatiles from the adsorbent. Microwave radiation energy can be applied to an adsorbent without heating a gas, and can effectively transfer thermal energy to specific adsorbents through path lengths in excess of 12 inches. To accomplish this method of heating the adsorbent media, the apparatus for applying or generating the microwave radiation for a heating device must be constructed in such a manner as to afford uniform heating of the adsorbent, and to minimize or eliminate any reflection of the radiation back onto the microwave power source 30. The microwave heating system 132 can include a heating apparatus and a heating or radiation system (not shown in FIG. 4), and optionally a purge gas system 124 (not shown in FIG. 4). The heating apparatus can be coupled to and in communication with the radiation system for receipt of thermal energy generated by the radiation system, such as microwave radiation or electromagnetic energy, and with the purge gas system 124 for receipt of a purge gas to assist in the removal of volatiles from the adsorbent.

Preferably the adsorbent used in the method of the present invention when loaded with hydrocarbons, is regenerated using a microwave regeneration system. Preferably, the microwave regeneration system is able to operate in a batch, semi-continuous, or continuous process. One advantage of using a microwave system in conjunction with adsorbents of the present invention is that it allows the microwaves to minimize the heating of the media, but maximize heating of the hydrocarbons to encourage desorption. As such it has the benefits of being operationally simpler than traditional regeneration systems, and reduces the heat effects on the adsorbent material itself. Furthermore, when this desorption process is used in conjunction with a continuous adsorption process such as a moving packed bed or similar device, the hydrocarbon removal can be closely tailored to the composition of the feed gas such that the recovered gas can have improved purity and, when present, reduced load on the subsequent chiller apparatus which allows for recovery and later transport as a liquid.

EXAMPLES

A description of the raw materials used in the Examples is as follows.

Example 1 is a porous cross-linked polymeric adsorbent having a high surface area equal to or greater than 1,000 m$^2$/g made from a macroporous copolymer of a monovinyl aromatic monomer and a crosslinking monomer, where the macroporous copolymer has been post-crosslinked in the swollen state in the presence of a Friedel-Crafts catalyst;

Example 2 is a porous cross-linked polymeric adsorbent having a surface area equal to or greater than 1,000 m$^2$/g made from a macroporous copolymer of a monovinyl aromatic monomer and a crosslinking monomer, where the macroporous copolymer has been post-crosslinked in the swollen state in the presence of a Friedel-Crafts catalyst with post capping of residual chloromethyl groups with hydrophobic aromatic compounds resulting in a media that has increased hydrophobicity; and Example 3 is a partially pyrolized macroporous polymer of a monovinyl aromatic monomer and a crosslinking monomer that has been sulfonated.

Adsorption capacity and breakthrough properties are determined for Example 1 and Example 2 as followed:
Adsorption Capacity
Methane, Ethane, Propane and Butane:

A Micromeritics ASAP 2020 Surface Area and Porosity Analyzer is used to analyze methane (Sigma-Aldrich, 99.0%), ethane (Sigma-Aldrich, 99.99), propane (Sigma-Aldrich, 99.97%), and butane (Matheson Tri-Gas, 99.9%) adsorption at 308 K. Prior to analysis, the macroporous polymeric adsorbent being tested (0.3 to 0.5 grams) is degassed in a quartz U-tube at 423 K under vacuum to a pressure below 5 µmHg for 12 hours. Pressure points are taken between 5 to 600 mmHg with a 45 seconds equilibration interval. The samples are then evacuated under vacuum for 1 hour before repeating the pressure points.
Pentane:

A Micromeritics ASAP 2020 Surface Area and Porosity Analyzer equipped with vapor introduction option with dual-zone temperature control is used to analyze static pentane adsorption at 273 K. An ethylene glycol/water mixture contained within a chiller dewer is used as temperature control for the sample. Pentane (Sigma-Aldrich, anhydrous, ≥99%) is placed in a quartz vessel located in the temperature-regulated vapor furnace which is controlled to 308K. Prior to pentane analysis, the macroporous polymeric adsorbent being tested is degassed in a quartz tube at 373 K under vacuum to a pressure below 5 µmHg for at least 12 hours. Relative pressure points are taken between 0.005<P/P$_0$<0.50. The saturation pressure, P$_0$, was calculated to be 183.526 mmHg based on pentane adsorptive properties and the analysis bath temperature.

Figure 7:
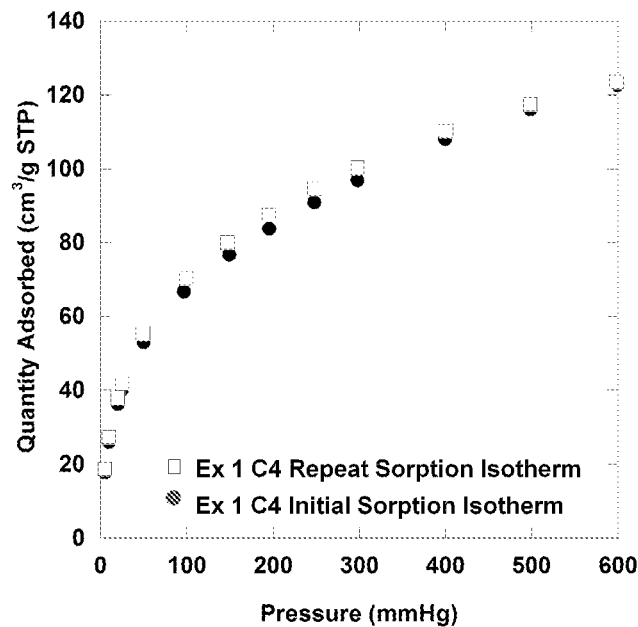
FIG. 7 shows the initial and repeat sorption isotherms for butane for Example 1.
Figure 8:
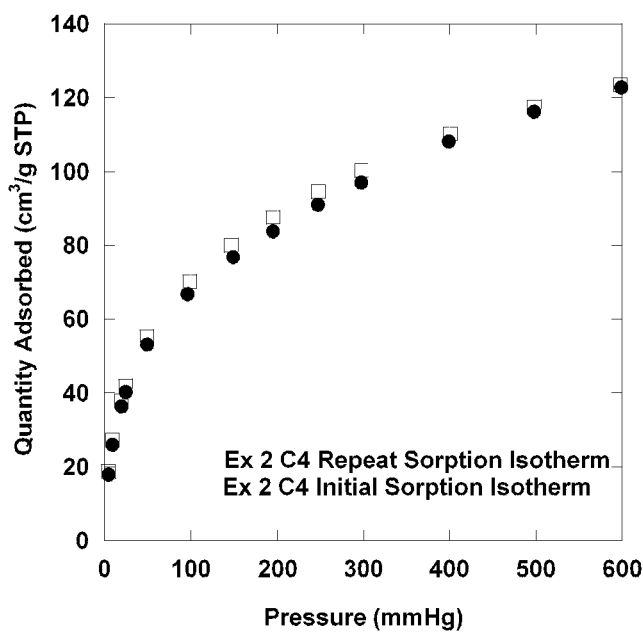
FIG. 8 shows the initial and repeat sorption isotherms for butane for Example 2.

FIGS. 7 and 8 show the initial and repeat adsorption isotherms for butane for Example 1 and Example 2, respectively.

Figure 9:
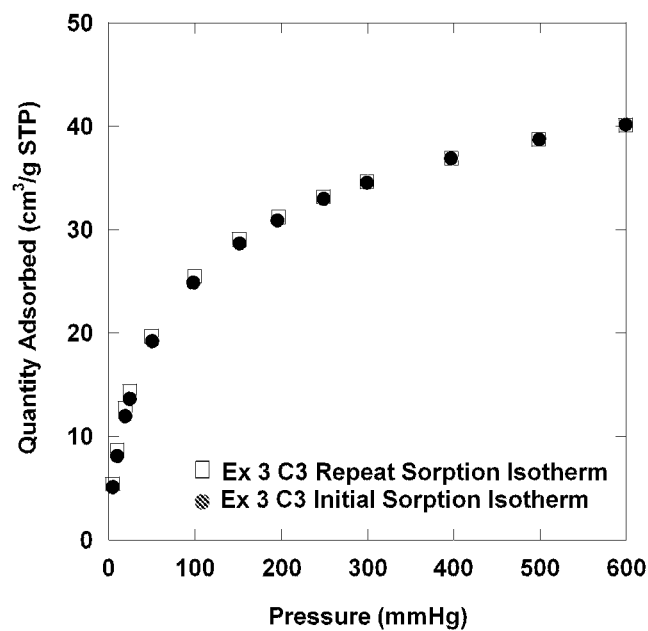
FIG. 9 shows the initial and repeat sorption isotherms for propane for Example 3.

FIG. 9 shows the initial and repeat adsorption isotherms for propane for Example 3.

Figure 10:
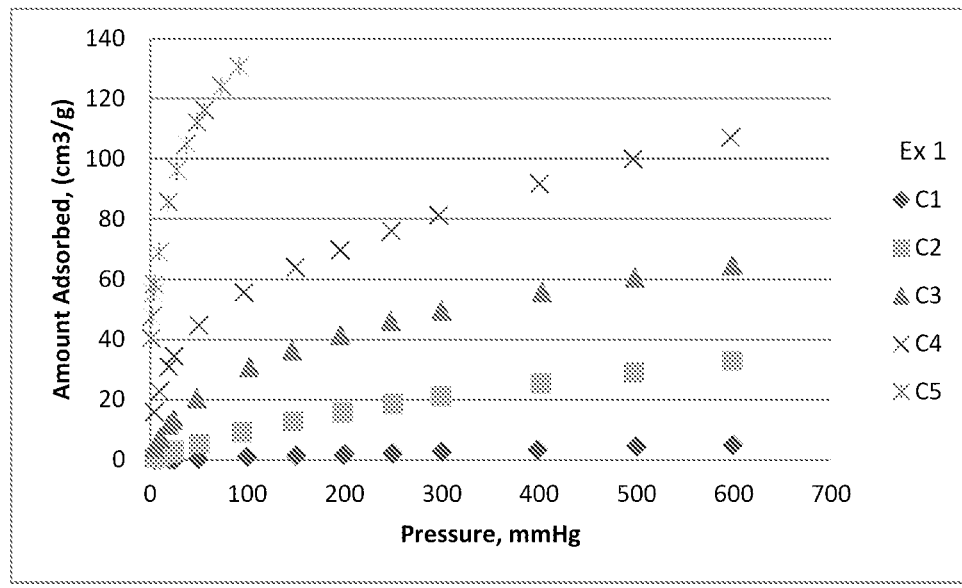
FIG. 10 shows the sorption isotherms for methane, ethane, propane, butane, and pentane for Example 1.
Figure 11:
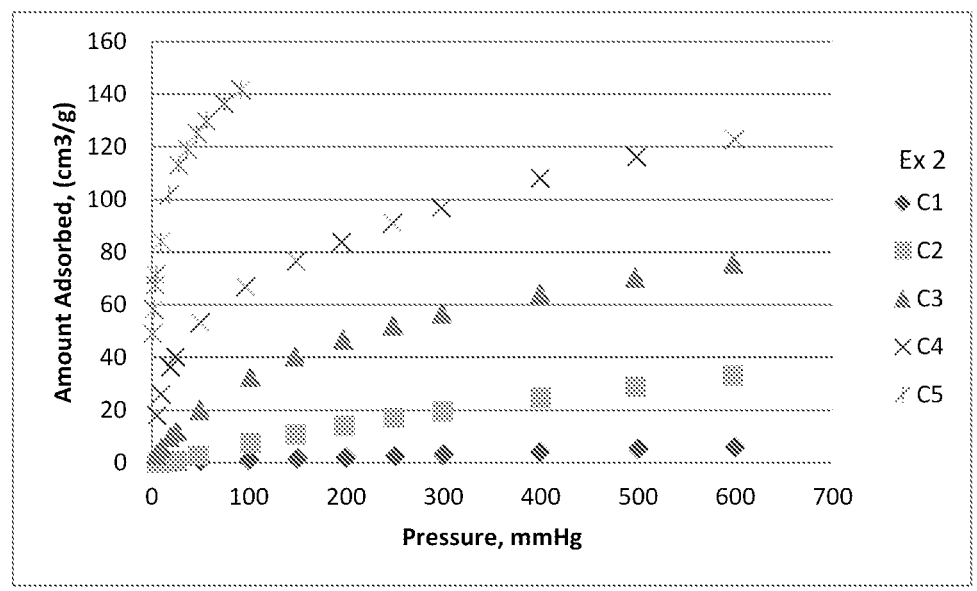
FIG. 11 shows the sorption isotherms for methane, ethane, propane, butane, and pentane for Example 2.
Figure 12:
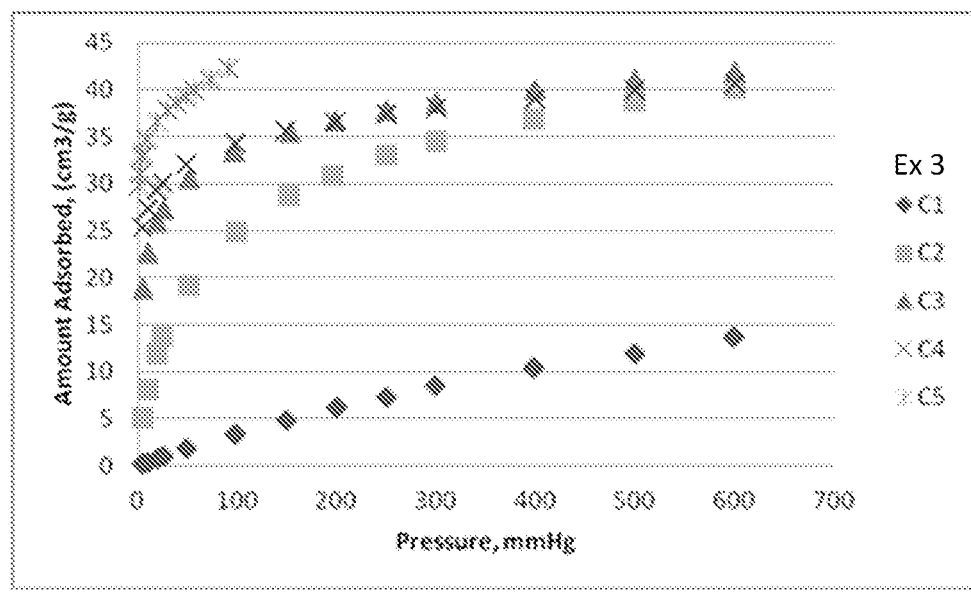
FIG. 12 shows the sorption isotherms for methane, ethane, propane, butane, and pentane for Example 3 an example of the present invention.

FIGS. 10, 11, and 12 show the adsorption isotherms for methane (C1), ethane (C2), propane (C3), butane (C4), and pentane (C5) for Examples 1, 2, and 3, respectively.
Adsorption Breakthrough Breakthrough curve data for the macroporous polymeric adsorbent is determined using a GC/mass spectrometer (mass spec). The GC/mass spec is calibrated then a 40 g sample is loaded into the sample column. A mixed gas comprising a ratio of $CH_4/C_2H_6/C_3H_8/C4H_{10}$ at 40/40/40/40 standard cubic centimeters per minute (SCCM) is analyzed. Gas flow is initiated. This flow by-passes the packed bed (i.e., column). The system is allowed to equilibrate for 2 hours. The gas from the by-pass is then analyzed by the mass spec. Following a two minute delay, the three-way valve is opened to allow the mixed gas to enter the packed bed column. The data for the mass spec analysis of the mixed gas leaving the packed bed column is recorded. The system is allowed to run until all four gases have been analyzed in the mass spec and recorded. Table 1 lists the breakthrough times for each gas.

TABLE 1

| Polymeric Sorbent Media | Example 1 | Example 2 | Example 3 |
|---|---|---|---|
| Weight, g | 40 | 40 | 40 |
| Volume, cc | 109 | 130 | 71 |
| Bulk Density, g/cc | 0.37 | 0.31 | 0.56 |
| Methane breakthrough, min | 5.2 | 6 | 6.3 |
| Ethane breakthrough, min | 13.2 | 16.5 | 11.1 |
| Propane Breakthrough, min | 27.3 | 33.2 | 16.4 |
| Butane breakthrough, min | 64 | 81.4 | 31.9 |

What is claimed is:

1. A carbon dioxide gas treating process, the process comprising:
   providing a carbon dioxide gas feedstream having one or more C1-C5 hydrocarbon;
   providing a first separation unit including a first adsorption unit and a first regeneration unit, the first adsorption unit including a first adsorption bed having a first adsorbent media that adsorbs the one or more C1-C5 hydrocarbon of the carbon dioxide gas feedstream, the first adsorbent media being a copolymer of one or more monoaromatic monomers and one or more nonaromatic monovinylidene monomers and being a porous cross-linked polymeric adsorbent that adsorbs a C3 hydrocarbon of the one or more C1-C5 hydrocarbon of the carbon dioxide gas feedstream, and the first regeneration unit including a microwave heating system;
   passing the carbon dioxide gas feedstream through the first adsorption unit at a first flow rate, and generating a loaded first adsorbent media including the one or more C1-C5 hydrocarbon of the carbon dioxide gas feedstream and a first treated carbon dioxide-rich gas stream;
   regenerating the loaded first adsorbent media in the first regeneration unit by releasing the one or more C1-C5 hydrocarbon of the carbon dioxide gas feedstream from the loaded first adsorbent media, forming regenerated first adsorbent media and released one or more C1-C5 hydrocarbon of the first adsorbent media and recovering, further separating, providing as fuel for a combustion process, flaring, or a combination thereof the released one or more C1-C5 hydrocarbon of the first adsorbent media;

providing the first treated carbon dioxide-rich gas stream to a second separation unit, the first treated carbon dioxide-rich treated gas stream having one or more C1-C5 hydrocarbon, the second separation unit including a second adsorption unit and a second regeneration unit, the second adsorption unit including a second adsorption bed having a second adsorbent media that is a pyrolyzed macroporous polymeric adsorbent that adsorbs a C2 hydrocarbon of the one or more C1-C5 hydrocarbon of the first treated carbon dioxide-rich gas stream and $CO_2$, and the second regeneration unit including a microwave heating system;

passing the first treated carbon dioxide-rich gas stream through the second adsorption unit at a second flow rate, and generating a second loaded adsorbent media including the one or more C1-C5 hydrocarbon of the first treated carbon dioxide-rich gas stream and a second treated carbon dioxide-rich gas stream;

regenerating the loaded second adsorbent media in the second regeneration unit by releasing the one or more C1-C5 hydrocarbon of the first treated carbon dioxide-rich treated gas stream from the loaded second adsorbent media, forming regenerated second adsorbent media and released one or more C1-C5 hydrocarbon of the second adsorbent media, and recovering, further separating, providing as fuel for a combustion process, flaring, or a combination thereof the released one or more C1-C5 hydrocarbon of the second adsorbent media;

providing the second treated carbon dioxide-rich gas stream to a third separation unit, the second treated carbon dioxide-rich treated gas stream including one or more C1-C5 hydrocarbon, recovering the C2 hydrocarbon of the one or more C1-C5 hydrocarbon of the second treated carbon dioxide-rich treated gas stream in the third separation unit, and the third separation unit including a condenser or a chiller;

liquefying the one or more C1-C5 hydrocarbon of the second treated carbon dioxide-rich gas stream, and generating one or more liquefied C1-C5 hydrocarbon and a third treated carbon dioxide-rich gas stream in the third separation unit;

recovering the one or more liquefied C1-C5 hydrocarbon for transportation, providing as fuel for a combustion process, for flaring, or a combination thereof; and providing the third carbon dioxide-rich gas stream to one or more additional separation unit for further treatment, injecting the third treated carbon dioxide-rich treated gas stream into an injection well, or a combination thereof.

2. The carbon dioxide gas treating process as claimed in claim 1, wherein the first adsorbent media is not the same as the second adsorbent media.

3. The carbon dioxide gas treating process as claimed in claim 1, wherein the first adsorbent media is independently regenerated by reduced pressure over the first adsorbent media, heating the first adsorbent media, or a combination of reduced pressure and heating of the first adsorbent media.

4. The carbon dioxide gas treating process as claimed in claim 1, wherein the first adsorbent media is a crosslinked macroporous polymer having a BET surface area of equal to or greater than 500 $m^2/g$ and a particle size of 300 microns to 1500 microns.

5. The carbon dioxide gas treating process as claimed in claim 4, wherein first adsorbent media is post-crosslinked in a swollen state in the presence of a Friedel-Crafts catalyst.

* * * * *